(12) United States Patent
Mickiewicz et al.

(10) Patent No.: US 10,842,541 B2
(45) Date of Patent: *Nov. 24, 2020

(54) INSTRUMENTS AND METHODS FOR TENSIONING A SPINAL TETHER

(71) Applicant: DEPUY SYNTHES PRODUCTS, INC., Raynham, MA (US)

(72) Inventors: Christopher Mickiewicz, Bridgewater, MA (US); John Riley Hawkins, Cumberland, RI (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/229,094

(22) Filed: Dec. 21, 2018

(65) Prior Publication Data

US 2019/0142481 A1    May 16, 2019

Related U.S. Application Data

(63) Continuation of application No. 15/158,696, filed on May 19, 2016, now Pat. No. 10,188,435, which is a continuation of application No. 14/693,929, filed on Apr. 23, 2015, now Pat. No. 9,370,390, which is a continuation of application No. 11/842,376, filed on Aug. 21, 2007, now Pat. No. 9,039,711.

(51) Int. Cl.
*A61B 17/70* (2006.01)
*A61B 17/88* (2006.01)
*A61B 17/56* (2006.01)

(52) U.S. Cl.
CPC ...... *A61B 17/7083* (2013.01); *A61B 17/7053* (2013.01); *A61B 17/8869* (2013.01); *A61B 17/701* (2013.01); *A61B 2017/564* (2013.01); *A61B 2017/567* (2013.01)

(58) Field of Classification Search
CPC ............ A61B 17/8861; A61B 17/8869; A61B 17/7083
See application file for complete search history.

(56) References Cited

U.S. PATENT DOCUMENTS 5,277,699 A    1/1994  Williamson
5,449,361 A    9/1995  Preissman
(Continued)

FOREIGN PATENT DOCUMENTS

WO    03049620 A1    6/2003

OTHER PUBLICATIONS

European Supplementary Search Report for Application No. 08796756.8 dated Jun. 22, 2012. (10 pages).
(Continued)

*Primary Examiner* — Julianna N Harvey
(74) *Attorney, Agent, or Firm* — Nutter McClennen & Fish LLP

(57) ABSTRACT

Various methods and devices are provided for tensioning a tether. In one embodiment, a tether tensioning device is provided and includes an elongate shaft adapted to be positioned adjacent to a bone anchor implanted in bone, and a tensioning mechanism pivotally associated with the elongate shaft and adapted to couple to a tether seated across the bone anchor and to pivot relative to the elongate shaft to apply a tensioning force to the tether.

12 Claims, 6 Drawing Sheets

(56) References Cited

U.S. PATENT DOCUMENTS

| | | | |
|---|---|---|---|
| 5,609,596 A * | 3/1997 | Pepper | A61B 17/8861 606/103 |
| 5,782,831 A | 7/1998 | Sherman et al. | |
| 5,902,305 A * | 5/1999 | Beger | A61B 17/8869 606/103 |
| 6,251,111 B1 | 6/2001 | Barker et al. | |
| 6,616,667 B1 * | 9/2003 | Steiger | A61B 17/8861 606/103 |
| 6,648,903 B1 | 11/2003 | Pierson, III | |
| 7,686,814 B2 * | 3/2010 | Lim | A61B 17/025 606/105 |
| 9,039,711 B2 | 5/2015 | Mickiewicz et al. | |
| 9,370,390 B2 | 6/2016 | Mickiewicz et al. | |
| 10,188,435 B2 | 1/2019 | Mickiewicz et al. | |
| 2003/0208203 A1 | 11/2003 | Lim et al. | |
| 2004/0138666 A1 * | 7/2004 | Molz, IV | A61B 17/88 606/74 |
| 2004/0215190 A1 | 10/2004 | Nguyen et al. | |
| 2005/0010220 A1 * | 1/2005 | Casutt | A61B 17/7008 606/86 A |
| 2005/0137608 A1 | 6/2005 | Hearn et al. | |
| 2006/0217714 A1 | 9/2006 | Serhan et al. | |
| 2006/0229623 A1 * | 10/2006 | Bonutti | A61B 17/0218 606/74 |
| 2009/0054933 A1 | 2/2009 | Mickiewicz et al. | |
| 2015/0223857 A1 | 8/2015 | Mickiewicz et al. | |

OTHER PUBLICATIONS

International Search Report for PCT/US08/071427, dated Oct. 22, 2008. (1 page).

International Preliminary Report on Patentability Chapter I for PCT/US08/071427, dated Mar. 4, 2010 (6 Pages).

* cited by examiner

INSTRUMENTS AND METHODS FOR TENSIONING A SPINAL TETHER

CROSS-REFERENCE TO RELATED APPLICATIONS

The present application is a continuation of U.S. application Ser. No. 15/158,696, filed May 19, 2016, which is a continuation of U.S. application Ser. No. 14/693,929 filed on Apr. 23, 2015 (now U.S. Pat. No. 9,370,390), which is a continuation of U.S. application Ser. No. 11/842,376 filed on Aug. 21, 2007 (now U.S. Pat. No. 9,039,711) each of which is incorporated herein by reference in its entirety.

FIELD

The present application relates to devices and methods for tensioning a tether extending between bone anchors implanted in bone.

BACKGROUND

Spinal deformities, which include rotation, angulation, and/or curvature of the spine, can result from various disorders, including, for example, scoliosis (abnormal curvature in the coronal plane of the spine), kyphosis (backward curvature of the spine), and spondylolisthesis (forward displacement of a lumbar vertebra). Early techniques for correcting such deformities utilized external devices that apply force to the spine in an attempt to reposition the vertebrae. These devices, however, resulted in severe restriction and in some cases immobility of the patient. Furthermore, current external braces have limited ability to correct the deformed spine and typically only prevent progression of the deformity. Thus, to avoid this need, several rod-based techniques were developed to span across multiple vertebrae and force the vertebrae into a desired orientation.

In rod-based techniques, one or more rods are attached to the vertebrae at several fixation sites to progressively correct the spinal deformity. The rods are typically pre-curved intraoperatively to a desired adjusted spinal curvature. Wires as well as bone screws can be used to pull individual vertebra toward the rod. Once the spine has been substantially corrected, the procedure typically requires fusion of the instrumented spinal segments.

While several different rod-based systems have been developed, they tend to be cumbersome, requiring complicated surgical procedures with long operating times to achieve correction. Further, intraoperative adjustment of rod-based systems can be difficult and may result in loss of mechanical properties due to multiple bending operations. The rigidity and permanence of rigid rod-based systems can also hinder or prevent growth of the spine and they generally require fusion of many spine levels, drastically reducing the flexibility of the spine. To help remedy some of these issues, a tether and anchor system can be used to correct curvature of the spine using a number of anchors disposed within the spinal bones connected with tethers extending between them. The elasticity of the tethers prevents some of the problems with the rigidity and permanence of the rod-based systems, although the tethers must be tensioned after implantation to achieve the desired force between the anchor to correct the spinal deformities.

Accordingly, there remains a need for improved methods and devices for correcting spinal deformities and, in particular, there remains a need for methods and devices for tensioning a tether extending between anchors implanted in bone.

SUMMARY

Various methods and devices for tensioning a tether are provided. In one embodiment, a tether tensioning device is provided and includes an elongate shaft adapted to be positioned adjacent to a bone anchor implanted in bone. A tensioning mechanism can be pivotally associated with the elongate shaft and it can be adapted to couple to a tether seated across the bone anchor and to pivot past a longitudinal axis of the elongate shaft to apply a tensioning force to the tether. In particular, the tensioning mechanism can be adapted to move from a first position in which the tensioning mechanism is pivoted away from the elongate shaft, to a second position in which the tensioning mechanism is pivoted past the longitudinal axis of the elongate shaft to apply a tensioning force to a tether. In one exemplary embodiment, the elongate shaft can include an elongate slot formed therein. The elongate slot can be adapted to receive the tensioning mechanism therethrough to facilitate pivoting of the tensioning mechanism past the longitudinal axis of the elongate shaft. Various techniques can be used to mate a tether to the tensioning mechanism. For example, the tensioning mechanism can include one or more openings formed therethrough and adapted to receive a portion of a tether to allow the tether to removably couple to the tensioning mechanism. The device can also include a handle coupled to a proximal end of the elongate shaft.

In one exemplary embodiment, the tensioning mechanism can also be adapted to move longitudinally along an axis of the elongate shaft between proximal and distal positions. The tether tensioning device can also include a biasing element coupled to the tensioning mechanism and adapted to bias the tensioning mechanism to the proximal position. For example, the biasing element can be a spring disposed within the elongate shaft and coupled to a distal portion of the tensioning mechanism to bias the tensioning mechanism proximally. The spring can be adapted to be compressed to allow the tensioning mechanism to move distally and to thereby control the amount of tensioning force applied to a tether as the tensioning mechanism is moved to the second position.

In another embodiment, a tether tensioning device is provided and includes an elongate shaft having a tensioning mechanism pivotally associated with the elongate shaft and adapted to couple to a tether to apply a tensioning force thereto. The device can also include an overload mechanism coupled to the tensioning mechanism. The overload mechanism can be adapted to allow the tensioning mechanism to move distally along an axis of the elongate shaft when a threshold force is applied to the tether. In one embodiment, the tensioning mechanism can be pivotally coupled to a body that is slidably coupled to the elongate shaft, and the overload mechanism can be a biasing element that biases the body proximally along the elongate shaft. In an exemplary embodiment, the overload mechanism can be in form of a spring disposed within the elongate shaft and coupled to a distal portion of the tensioning mechanism. The spring can be adapted to be compressed by the tensioning mechanism when a threshold force is applied to a tether coupled to the tensioning mechanism. In order to apply the tensioning force to the tether, the tensioning mechanism can be adapted to move from a first position in which the tensioning mechanism is pivoted away from the elongate shaft, to a second position in which the tensioning mechanism is pivoted past a longitudinal axis of the elongate shaft to apply a tensioning force to a tether. In one embodiment, the tensioning mechanism can include one or more openings formed therethrough for receiving a portion of the tether therethrough to allow the tether to removably couple to the tensioning mechanism.

Methods for applying tension to a tether are also provided, and in one embodiment the method can include coupling a tether seated across a bone anchor implanted in bone to a tensioning mechanism pivotally associated with an elongate shaft, and pivoting the tensioning mechanism past a longitudinal axis of the elongate shaft to apply a tensioning force to the tether. Coupling the tether to the tensioning mechanism can include threading a portion of the tether through one or more openings formed in the tensioning mechanism. Pivoting the tensioning mechanism can include moving the tensioning mechanism from a first position in which the tensioning mechanism is pivoted away from the elongate shaft, to a second position in which the tensioning mechanism is pivoted past the longitudinal axis of the elongate shaft to apply the tensioning force to the tether. In one exemplary embodiment, the tensioning mechanism is pivoted past the longitudinal axis of the elongate shaft by pivoting into a slot formed in the elongate shaft. The tensioning mechanism can optionally be biased to a proximal position by a biasing element coupled to a distal end of the tensioning mechanism. When a threshold tensioning force is applied to the tether, the tensioning mechanism moves distally along a longitudinal axis of the elongate shaft. In one embodiment, a biasing element can bias the tensioning mechanism proximally, and the biasing element can be compressed as the tensioning mechanism moves distally.

BRIEF DESCRIPTION OF THE DRAWINGS

Various exemplary embodiments disclosed herein will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope of the present application.

Various exemplary methods and devices are provided for tensioning a tether extending across one or more anchors implanted in bone. In general, a tensioning mechanism is provided that is adapted to couple to a tether seated across one or more bone anchors implanted in bone. The tensioning mechanism can be adapted to apply a tensioning force to the tether to allow the tether to be tensioned between the bone anchors.

Figure 1:
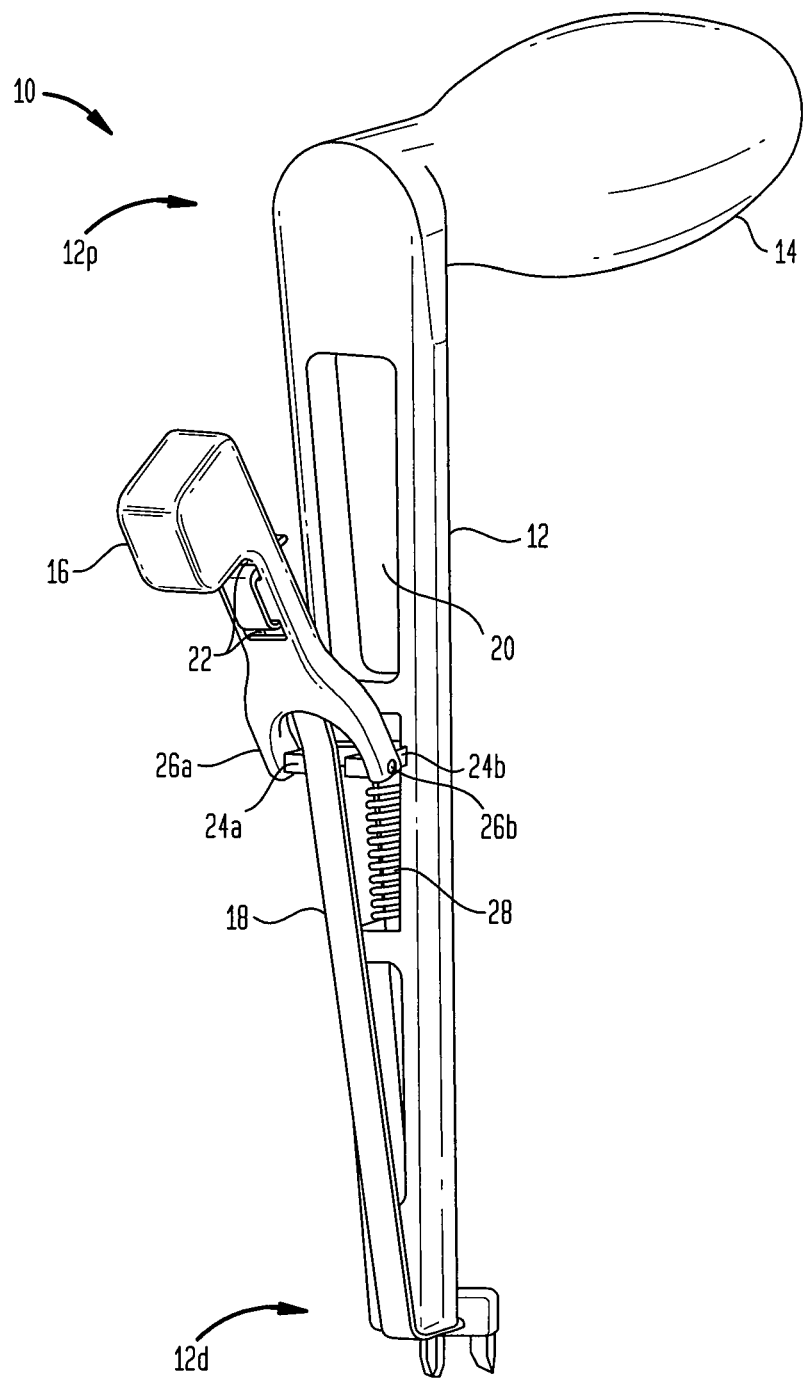
FIG. 1 is a perspective view of one embodiment of a tether tensioning device having a tensioning mechanism shown in a first, untensioned position.
Figure 2:
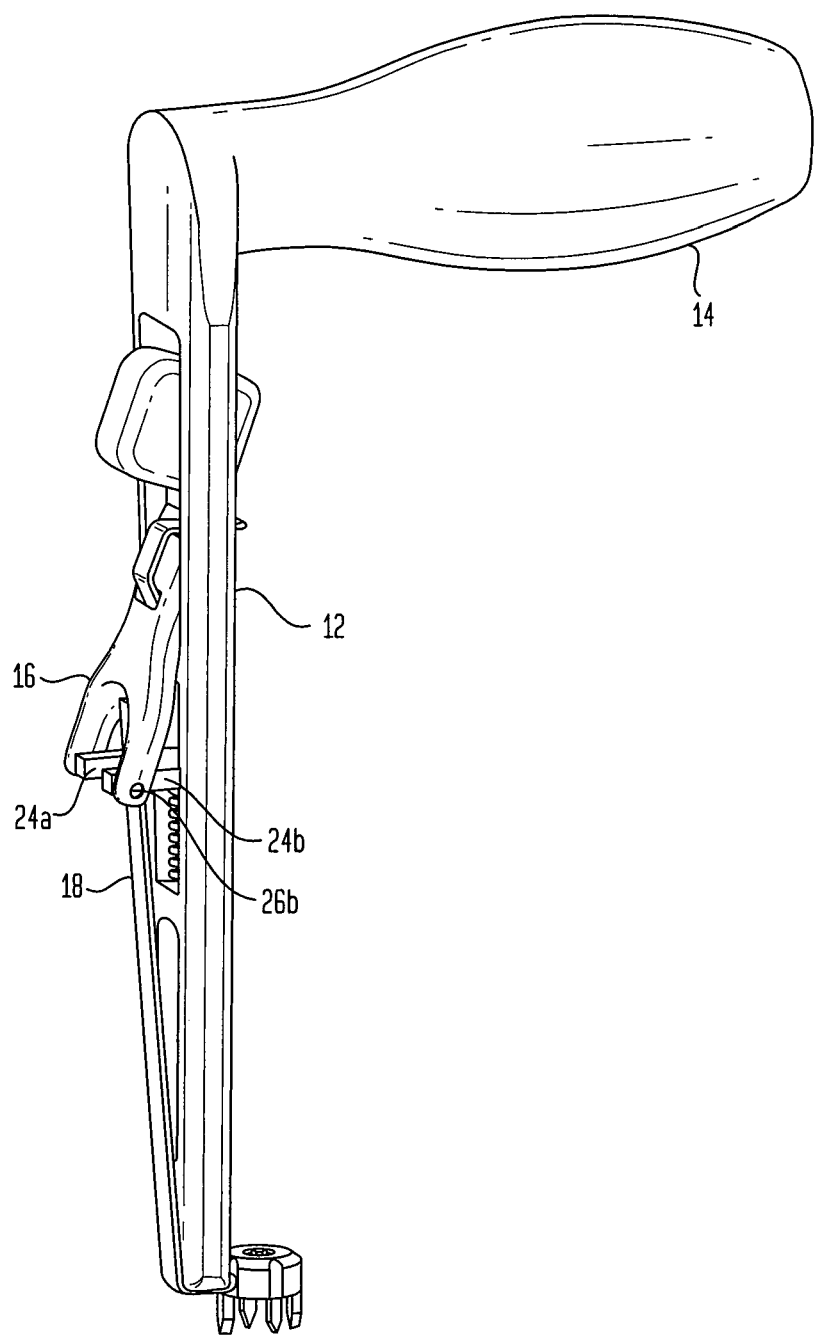
FIG. 2 is a perspective view of the tether tensioning device of FIG. 1 showing the tensioning mechanism in a second, tensioned position.
Figure 3:
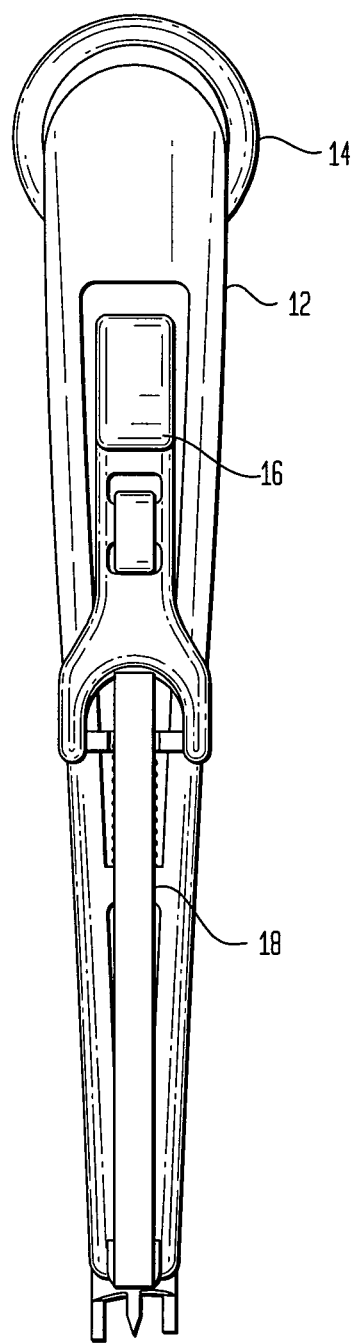
FIG. 3 is a front view of the tether tensioning device of FIG. 2.

FIGS. 1-3 illustrate one exemplary embodiment of a tether tensioning device 10 that generally includes an elongate shaft 12 extending from a handle 14. A tensioning mechanism 16 is pivotally associated with the elongate shaft 12 and it is adapted to mate to a tether 18 seated across one or more bone anchors implanted in bone. The tensioning mechanism 16 can be adapted to move from a first, untensioned position in which the tensioning mechanism 16 is pivoted away from the elongate shaft 12, shown in FIG. 1, to a second, tensioned position in which the tensioning mechanism 16 is pivoted toward the elongate shaft 12 and past a longitudinal axis of the elongate shaft 12 to apply a tensioning force to the tether 18. In one exemplary embodiment, the tensioning mechanism 16 can be pivoted into a slot 20 formed in the elongate shaft 12 to apply a tensioning force to the tether 18, shown in FIG. 2. A person skilled in the art will appreciate that the tensioning mechanism 16 can be pivoted past the longitudinal axis of the elongate shaft 12 in a variety of ways, including but not limited to the tensioning mechanism 16 being moved around a side of the elongate shaft 12, over an end of the elongate shaft 12, or up into the elongate shaft 12.

The elongate shaft 12 can have a variety of configurations, and it can be flexible or rigid depending on the intended use. In an exemplary embodiment, the elongate shaft 12 has a length that allows the distal end 12d of the elongate shaft 12 to be positioned adjacent to a tether 18 disposed along a spinal column, while the proximal end 12p remains external to the body. This length allows the elongate shaft 12 to extend from the tissue surface to the treatment site, e.g., bone anchors implanted in vertebrae. A person skilled in the art will appreciate that the elongate shaft 12 can be made from a variety of biocompatible materials that have properties sufficient to enable the elongate shaft 12 to be inserted into the body. As further shown in FIGS. 1-3, the elongate shaft 12 can also include a slot 20 formed therein. The slot 20 can be configured to receive a portion of the tensioning mechanism 16 when the tensioning mechanism 16 is moved to the second position, as will be discussed in more detail below. Thus, the particular location and size of the slot 20 can vary depending on the location and size of the tensioning mechanism 16. In the illustrated embodiment, the slot 20 is located in a proximal portion of the elongate shaft 12, just proximal to the mating location between the tensioning mechanism 16 and the elongate shaft 12, and it extends along about half or less than half of the length of the elongate shaft 12. A person skilled in the art will appreciate that the slot 20 can have various configurations and it can be at a variety of locations on the elongate shaft 12.

The elongate shaft 12 can also include a handle 14 formed on or coupled to the proximal end 12p of the elongate shaft 12. The handle 14 can have any shape and size but it is preferably adapted to facilitate grasping and manipulation of the device 10. As shown in FIG. 1, the handle 14 has a generally elongate cylindrical configuration and extends substantially perpendicular to the longitudinal axis of the elongate shaft 12. A person skilled in the art will appreciate that any handle can be coupled to the elongate shaft, or that the device 10 can be used without a handle.

Figure 4:
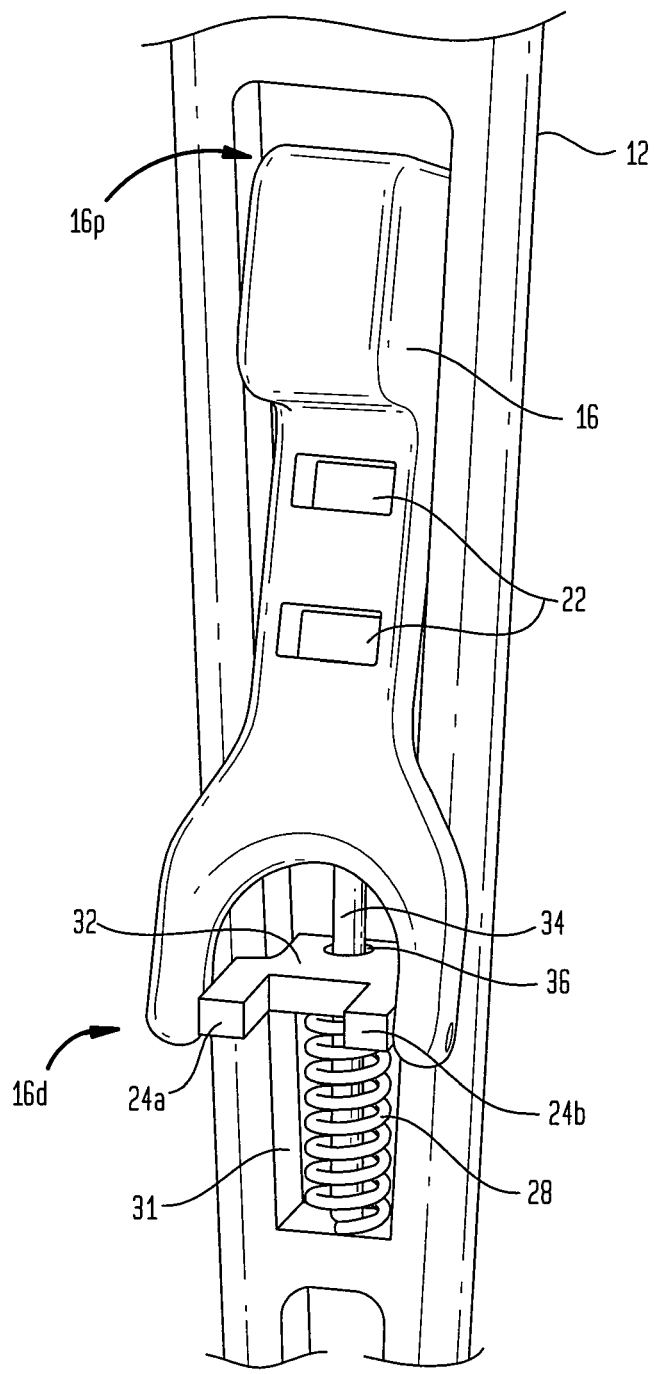
FIG. 4 is a perspective view of the tether tensioning device of FIG. 2 showing a biasing element coupled to the tensioning mechanism.
Figure 5:
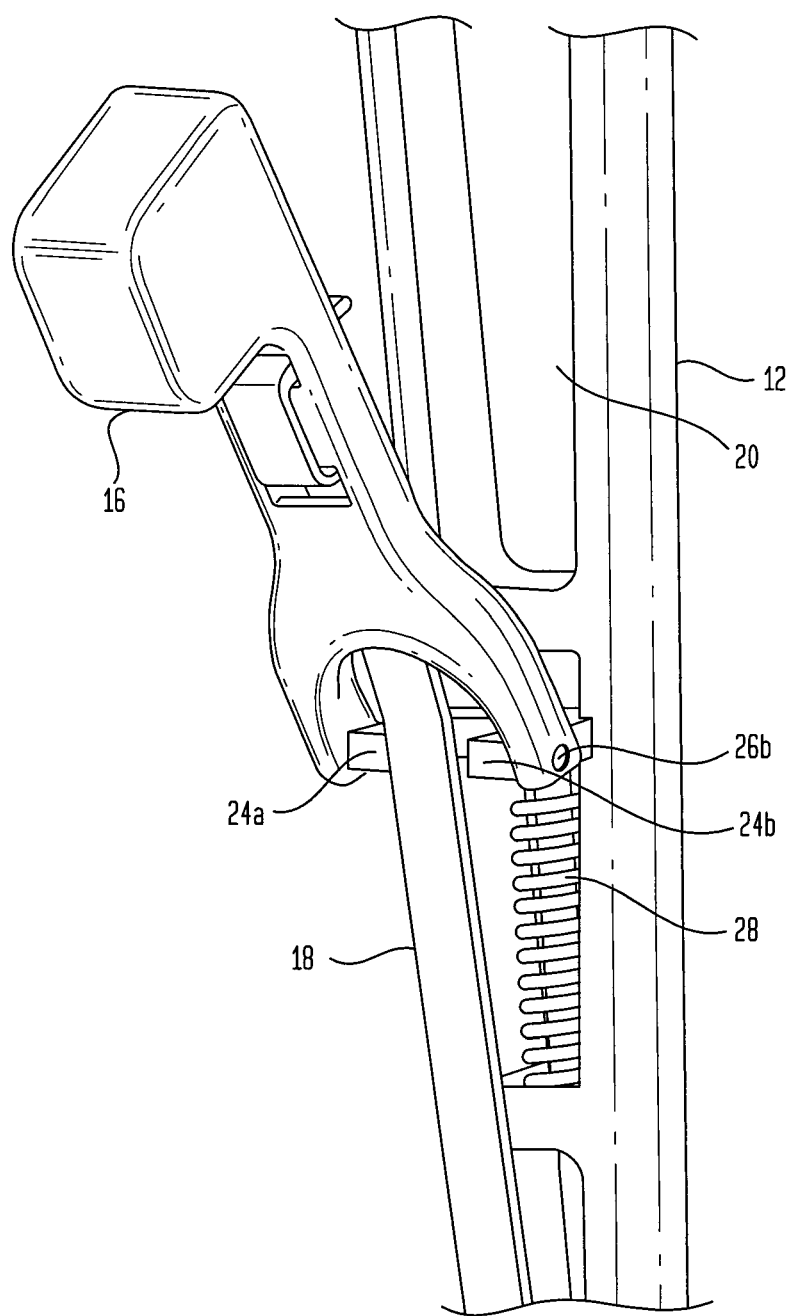
FIG. 5 is a perspective view of the tensioning mechanism and biasing element of FIG. 4 showing a tether coupled to the tensioning mechanism that is in the first, untensioned position.
Figure 6:
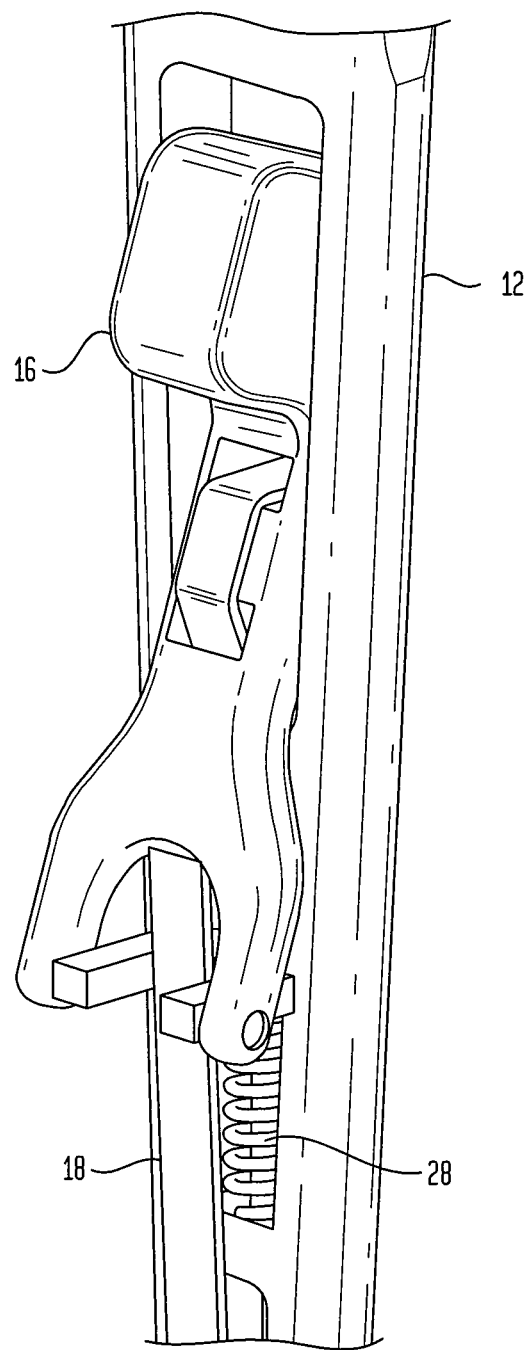
FIG. 6 is a perspective view of the tensioning mechanism and biasing element of FIG. 4 showing a tether coupled to the tensioning mechanism that is in the second, tensioned position.

As indicated above, the device 10 also includes a tensioning mechanism 16, shown in more detail in FIGS. 4-6, that is associated with the elongate shaft 12 and that is adapted to apply a tensioning force to a tether 18. The tensioning mechanism 16 can have a variety of shapes and sizes, but it is preferably adapted to grasp or mate to a tether 18 and to apply a tensioning force to the tether 18. While the tensioning mechanism 16 can have a variety of configurations, in one exemplary embodiment, as shown, the tensioning mechanism 16 is in the form of an arm that is pivotally coupled to the elongate shaft 12. The tensioning mechanism 16 can be pivotally coupled to the elongate shaft in a variety of ways. For example, in the illustrated embodiment, a distal end 16d of the tensioning mechanism 16 includes two legs that are pivotally coupled to first and second pivot bosses 24a, 24b disposed on the elongate shaft 12 at first and second pivot points 26a, 26b. The bosses 24a, 24b are located just distal to a distal end of the elongate slot 20. A person skilled in the art will appreciate, however, that the tensioning mechanism 16 can be coupled to the elongate shaft 12 in any way that allows it to pivot with respect to the elongate shaft 12. Moreover, a person skilled in the art will appreciate that the tensioning mechanism 16 can be removable from the elongate shaft 12. The tensioning mechanism 16 can be pivotally attached to the elongate shaft 12 in a variety of ways, including nesting the tensioning mechanism 16 into the elongate shaft 12, or coupling the tensioning mechanism 16 to the bosses 24a, 24b disposed on the elongate shaft 12. In addition, the tensioning mechanism 16 can be positioned along the elongate shaft 12 at a variety of locations, but it is preferably positioned at a location that allows the tensioning mechanism 16 to be pivoted into the elongate slot 20, and that allows the tensioning mechanism 16 to be manipulated by a user when the distal end of the elongate shaft 12 is positioned adjacent to a tether 18 implanted in the spine.

The tensioning mechanism 16 can also include features to allow the tether 18 to be coupled thereto. In one embodiment, the tensioning mechanism 16 can include one or more openings 22 formed therethrough. The openings 22 can have any size and shape, but are preferably of a size and shape that facilitate threading the tether 18 therethrough. A person skilled in the art will appreciate that any features can be used to couple the tether 18 to the tensioning mechanism 16, including any type of opening or grasping mechanism formed on the tensioning mechanism 16. In one embodiment, where the tensioning mechanism 16 is removable from the elongate shaft 12, the tether 18 can be pulled to the correct length by hand, and then coupled to the tensioning mechanism 16, for example, through the openings 22.

In order to apply the tensioning force to the tether 18, the tensioning mechanism 16 is adapted to pivot from a first, untensioned position in which the tensioning mechanism 16 is spaced apart from and extends transverse to the elongate shaft 12, as shown in FIG. 1, to a second, tensioned position in which the tensioning mechanism is pivoted into the slot 20 to apply a tensioning force to a tether 18. In particular, as the tensioning mechanism 16 is moved to the second position, the tether 18 is pulled proximally and then pulled through the slot 20. In order to maintain the tensioning force applied to the tether 18 when the tensioning mechanism 16 is pivoted into the second, tensioned position, the tensioning mechanism 16 can be adapted to pivot in such a way as to allow at least a portion of the tensioning mechanism 16 to extend completely through the slot 20 formed in the elongate shaft 12, as shown in FIG. 2. In other words, the tensioning mechanism 16 moves across the longitudinal axis and is positioned on an opposite side of the elongate shaft 12. As a result, a portion of the tether 18 coupled to the tensioning mechanism 16 is positioned past the pivot points 26a, 26b and is being pulled with a downward force. This downward force maintains the tensioning mechanism 16 in the second, tensioned positioned, thus maintaining the tensioning force applied to the tether 18. A person skilled in the art will appreciate that a variety of other techniques can be used to maintain the tensioning mechanism 16 is the second position, including various locking mechanisms.

The tensioning mechanism 16 can also includes features to control the amount of tensioning force that is applied to the tether 18. In the illustrated embodiment, an overload mechanism is coupled to the tensioning mechanism 16 and it is adapted to allow the tensioning mechanism 16 to move distally along an axis of the elongate shaft 12 between a proximal position and distal position when a threshold force is applied to the tether 18. This prevents a tensioning force greater than the threshold force from being applied to the tether 18.

The overload mechanism can have a variety of configurations, but in one embodiment it can be in the form of a biasing element, such as a spring 28, for biasing the tensioning mechanism 16 proximally. The spring 28 can be disposed in a channel 31 formed in the elongate shaft 12, preferably at a position distal of the elongate slot 20. A proximal end of the spring 28 can be coupled to a distal end of the tensioning mechanism 16, and in particular the proximal end of the spring 28 can abut against a distal surface of a body 32 have the bosses 24a, 24b formed thereon. The body 32 can be movably disposed within the channel 31. In order to maintain the body 32 and the spring 28 in the channel 31, the channel 31 can include an elongate rod 34 disposed therein and extending through the spring 28 and through a bore 36 in the body 32. This will allow the body 32, and thus the tensioning mechanism 16, to move proximally and distally within the channel 31, thereby compressing and relieving the spring 28. A distal end of the spring 28 can rest against a distal portion of the channel 31 formed in the elongate shaft 12. In use, the biasing force of the spring 28 on the tensioning mechanism 16 can be overcome by pivoting the tensioning mechanism 16 until the tensioning force being applied to the tether 18 reaches the threshold force. This causes the tensioning mechanism 16 to move distally and thereby compress the spring 28, thus preventing any additional tensioning force from being applied to the tether 18. The tension of the spring 28 can be selected based on the desired threshold force. For example, a tightly-wound spring will yield a higher threshold force than a loosely-wound spring. A person skilled in the art will appreciate that a variety of other biasing elements can be used to control the amount of tensioning force being applied to the tether 18.

In use, the device 10 can be inserted through tissue, or through an access port disposed in tissue, so that the handle 14 and the tensioning mechanism 16 can extend from the tissue or port on the outside, and the distal end of the device 10 can be positioned adjacent to a bone anchor. The device 10 can be positioned adjacent to a tether 18 extending between bone anchors to be tensioning. For example, the device 10 can be removably mated to the bone anchor, or it can be positioned against a side of the bone anchor, or spaced apart from the bone anchor. A free end of the tether 18 can be grasped using a grasping device to allow the tether 18 to be removed from the body and coupled to the tensioning mechanism 18, as shown in FIG. 5. Once the tether 18 is coupled to the tensioning mechanism 16, the tensioning mechanism 16 can be pivoted towards the elongate shaft 12 and into and through the slot 20 to cause a tensioning force to be applied to the tether 18, as shown in FIG. 6. If the tensioning force being applied to the tether 18 reaches a threshold force based on the tension of the spring 28 coupled to the tensioning mechanism 16, the spring 28 will collapse, allowing the tensioning mechanism 16 to move distally along the elongate shaft 12. This is effective to prevent the tensioning force being applied to the tether 18 from being greater than the threshold force.

Once the proper tension is applied to the tether 18, and the tether 18 has been locked to the bone anchor(s) to retain the tension thereon after the device 10 is removed, the device 10 can be removed. In one embodiment, the tether can be locked between adjacent bone anchors by applying a locking mechanism, such as a set screw, to each bone anchor. A person skilled in the art will appreciate that any mechanism can be used to lock the tensioned tether 18 between adjacent bone anchors.

A person skilled in the art will appreciate that the various methods and devices disclosed herein can be formed from a variety of materials. Moreover, particular components can be implantable and in such embodiments the components can be formed from various biocompatible materials known in the art. Exemplary biocompatible materials include, by way of non-limiting example, composite plastic materials, biocompatible metals and alloys such as stainless steel, titanium, titanium alloys and cobalt-chromium alloys, and any other material that is biologically compatible and non-toxic to the human body.

One skilled in the art will appreciate further features and advantages based on the above-described embodiments. Accordingly, the disclosure is not to be limited by what has been particularly shown and described, except as indicated by the appended claims. All publications and references cited herein are expressly incorporated herein by reference in their entirety.

The invention claimed is:

1. A method of applying a tensioning force to a tether extending along a spinal column, comprising:
coupling a tether seated across a bone anchor implanted in bone to a tensioning arm pivotally associated with an elongate shaft; and
pivoting the tensioning arm from a first side of a longitudinal axis of the elongate shaft to a second side of the longitudinal axis to apply a tensioning force to the tether,
wherein, when a threshold tensioning force is applied to the tether, the tensioning arm moves distally along a longitudinal axis of the elongate shaft.

2. The method of claim 1, wherein coupling the tether to the tensioning arm includes threading a portion of the tether through one or more openings formed in the tensioning arm.

3. The method of claim 1, wherein the tensioning arm is pivoted past the longitudinal axis of the elongate shaft by pivoting into a slot formed in the elongate shaft.

4. The method of claim 1, wherein a biasing element biases the tensioning arm proximally, and the biasing element is compressed as the tensioning arm moves distally.

5. The method of claim 1, wherein the tensioning arm is moveable from a first position in which the tensioning arm is pivoted away from the elongate shaft, to a second position in which the tensioning arm is pivoted past the longitudinal axis of the elongate shaft to apply the tensioning force to the tether.

6. The method of claim 1, wherein the tensioning arm is pivotally connected to a plate such that the pivot point of the tensioning arm is offset from the elongated shaft.

7. The method of claim 6, wherein the plate is moveable longitudinally along an axis of the elongate shaft between proximal and distal positions.

8. The method of claim 7, further comprising a biasing element coupled to the plate and adapted to bias the plate to the proximal position.

9. The method of claim 8, wherein the biasing element comprises a spring disposed within the elongate shaft and coupled to the plate to allow the plate to move longitudinally along a portion of the elongate shaft.

10. The method of claim 9, wherein the spring is adapted to be compressed to control the amount of tensioning force applied to the tether as the tensioning arm is pivoted.

11. The method of claim 6, wherein the plate includes two opposed arms and the tensioning arm is pivotally connected to the two opposed arms.

12. The method of claim 6 wherein the plate is slidably coupled to a rod disposed in the elongate shaft such that the rod guides the plate within the elongate shaft.

* * * * *